United States Patent [19]

Wagner et al.

[11] Patent Number: 5,079,150
[45] Date of Patent: Jan. 7, 1992

[54] HIGH SENSITIVITY DETECTION OF PEROXIDASE ACTIVITY

[75] Inventors: Daniel B. Wagner, Raleigh; Glen P. Vonk, Fuquay-Varina; Randy A. Hoke, Cary, all of N.C.

[73] Assignee: Becton, Dickinson and Company, Franklin Lakes, N.J.

[21] Appl. No.: 272,360

[22] Filed: Nov. 17, 1988

[51] Int. Cl.$^5$ .................. C12Q 1/00; C12Q 1/28; G01N 33/53
[52] U.S. Cl. .................. 435/79; 435/792; 435/794; 435/28; 435/805; 435/970
[58] Field of Search .............. 435/27, 28, 805, 25, 435/7.9, 7.92, 7.94, 970; 436/66; 564/442, 305

[56] References Cited

U.S. PATENT DOCUMENTS 4,016,043 4/1977 Schuurs et al. .
4,416,982 11/1983 Tsuda et al. .................. 435/25

FOREIGN PATENT DOCUMENTS 0219352 10/1985 European Pat. Off. .

OTHER PUBLICATIONS

Tarcha, Peter J. et al., 2,3-Diaminophenazine is the Product from the Horseradish Peroxidase-Catalyzed Oxidation of o-Phenylenediamine, Analytical Biochemistry, 165, 230-233 (1987).

Primary Examiner—Robert J. Warden
Assistant Examiner—Jacintha M. Stall
Attorney, Agent, or Firm—Richard E. Brown

[57] ABSTRACT

A new class of peroxidase substrates consists of o-diaminobenzenes having a substituent in the 4 position. The new substrates may be used in immunoassays in which a peroxidase is the label, or in assays for the peroxidase itself. Immunoassays using other enzyme labels which cause formation of hydrogen peroxide may be followed using the substrate of the invention by adding the substrate and a peroxidase to the assay fluid and detecting color formed as a result of oxidation of the substrate by the formed peroxide.

9 Claims, No Drawings

HIGH SENSITIVITY DETECTION OF PEROXIDASE ACTIVITY

1. FIELD OF THE INVENTION

This invention relates to immunoassay of an analyte and materials used therein, and more particularly relates to a method and materials for immunoassay using a novel peroxidase substrate.

2. Background of the Invention

Assay systems which are both rapid and sensitive have been developed to determine the concentration of a substance in a fluid. Immunoassays depend on the binding of an antigen or hapten to a specific antibody and have been particularly useful because they give high levels of specificity and sensitivity. These assays generally employ one of the above reagents in labeled form, the labeled reagent often being referred to as the tracer. Immunoassay procedures may be carried out in solution or on a solid support and may be either heterogeneous, requiring a separation of bound tracer from free (unbound) tracer or homogeneous in which a separation step is not required.

Enzymes have often been used as labels in immunoassay. In conventional enzyme immunoassay (EIA), an enzyme is covalently conjugated with one component of a specifically binding antigen antibody pair, and the resulting enzyme conjugate is reacted with a substrate to produce a signal which is detected and measured. The signal may be a color change, detected with the naked eye or by a spectrophotometric technique, or may be conversion of the substrate to a product detected by fluorescence.

A class of enzymes commonly used as labels in EIA are the peroxidases. Peroxidases catalyze the oxidation of a substrate to a product by hydrogen peroxide. Horseradish peroxidase (HRP) is a widely used example of this class of enzymes. U.S. Pat. No. 4,016,043 to Schuurs et al. discloses EIA using HRP.

Numerous substrates oxidized by hydrogen peroxide under catalysis by a peroxidase are known. Among the more common are 3,3'-diaminobenzidine (DAB), 5-amino salicylic acid, (5AS) o-dianisidine, o-toluidine and, most commonly, o-phenylenediamine (OPD). Tarcha et al., Analytical Biochemistry, 165, 30 (1987) have reported that the oxidation of OPD with peroxide, in the presence or absence of HRP, gives 2,3 diaminophenazine, and that this product in water binds strongly to sulfonated polystyrene but is subsequently displaced from the polystyrene surface by sodium dodecyl sulfate solutions.

Known substrates, while useful, have certain limitations. For example, the oxidation product of OPD has sufficient water solubility so that it gives an excellent visual readout in a solution assay. On the other hand, the water solubility of the oxidation product causes rapid diffusion when the product is deposited as a spot on a solid phase, such as a membrane or dipstick. This severely reduces assay sensitivity and limits usefulness of OPD in ELISA procedures.

Several substrates which generate insoluble products are known, such as DAB, 3-amino-9-ethylcarbazole, 3,3',5,5'-tetramethylbenzidine, and 4-chloro-1-naphthol. While effective, these substrates do not generate as much color as is developed with OPD and peroxidase.

There is a need for a peroxidase substrate which enters an oxidation reaction with peroxide to give a product of sufficiently low solubility to form a stable, well-defined and deeply colored spot on a membrane or dipstick. It is toward fulfillment of this need that this application is directed.

SUMMARY OF THE INVENTION

One aspect of the present invention is a new class of peroxidase substrates comprising o-diaminobenzenes having a substituent in the 4 position. The substrates of the invention are rapidly oxidized by peroxide in the presence of peroxidase to from stable, deeply colored spots on membranes or deep colors in solution. Preferred substrates are alkyl or halo substituted o-diaminobenzenes, such as 3,4-diaminotoluene, (DAT). The preferred peroxidase is HRP.

In another aspect of the invention, the new substrates are used in an immunoassay in which a peroxidase is the label. Preferred immunoassays of the invention are solid phase assays performed on a membrane. The most preferred assay is a sandwich assay in which an antibody is affixed to a membrane and contacted with an antigen and a second antibody having HRP covalently conjugated thereto.

The substrates of the invention may also be used in assays to detect a peroxidase in a solution by detecting color when the solution is contacted with the substrate and peroxide. In still another embodiment of the invention, the substrate of the invention may be used in any assay in which peroxide is generated and released into assay fluid. In this type of assay, peroxide is the product of an enzymatic reaction, and measurement of the peroxide using the substrate of the invention provides a means of following the enzymatic reaction.

When a peroxidase based assay is performed on a membrane using the substrate of the invention, a stable, deeply colored spot is formed. The spot is formed within a few minutes and, because it is substantially water insoluble, does not wash off the membrane. For this reason, the substrate of the invention is particularly useful in flow through assays where the conventional substrate, OPD, is almost useless because its oxidation product, diaminophenazine, has sufficient solubility that diffuse, poorly defined spots are obtained.

With the new substrate, it is possible to visually detect HRP and its conjugates at a significantly higher sensitivity than with any heretofore reported peroxidase substrate known to the applicants. This high visual sensitivity of HRP on membranes may lead to the development of simple immunoassay devices with visual non instrumental readout particularly suitable to use in a physician's office, or even in the home.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

The invention provides a new substrate for a peroxidase and a method for use of the substrate in an immunoassay of an analyte in a liquid in which a peroxidase serves as the label. The invention also includes a method for determining a peroxidase or peroxide in a liquid. (In this disclosure, "determining" means detecting the analyte, peroxidase or peroxide in the liquid, i.e., its presence or absence, or measuring its concentration in the liquid.)

The invention will be described in terms of HRP, which is the preferred peroxidase because of its ready availability and its high enzymatic activity. However, it is understood that the substrate and assay methods of the invention will be equally useful with any other peroxidase.

The substrate of the invention is a 4-substituted or 4,5-disubstituted diaminobenzene of the following formula:

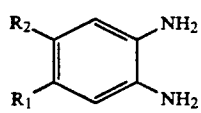

wherein $R_1$ is a lower alkyl group of 1 to 6 carbon atoms or a halogen atom, such as a chloro or fluoro group, and $R_2$ is hydrogen or $R_1$. In preferred substrates of the invention, $R_1$ is chloro or a lower alkyl group of 1 to 3 carbon atoms and $R_2$ is hydrogen or $R_1$. The most preferred substrates are DAT and 4-chloro- 1,2-phenylenediamine.

The new peroxidase substrates of the invention are known compounds which are either commercially available or may be prepared by conventional methods well known in the art.

Immunoassay procedures in which a peroxidase catalyzes the oxidation of a substrate by peroxide are well known in the art, and any immunoassay procedure which includes the substrate of the invention is contemplated to fall within the scope of the invention. In general, the immunoassay of the invention may be used to determine an antigen, an antibody or a hapten. In this disclosure, the substance to be determined is referred to as the analyte. The only limitation on the analyte is that it must be possible to obtain an antianalyte which binds substantially specifically to the analyte. Thus, if the analyte is an antigen, a suitable antianalyte would be a specific antibody. If the analyte is a hapten, a suitable antianalyte would be an antihapten antibody. If the analyte is an antibody, a suitable antianalyte would be a specific anti antibody. Antibodies useful in the invention as antianalytes may be either monoclonal or polyclonal. Raising of specifically binding antibodies is well known in the art and no further description is needed for a full understanding of the invention.

The immunoassay of the invention may be carried out by any conventional sandwich or competitive procedure as known in the art. The assay may be either heterogeneous or homogeneous, and may be carried out in the liquid phase or on a solid support. For example, in a typical sandwich assay, a first antibody may be affixed to a solid support such as a dipstick, membrane, microtiter plate well or the inside wall of a tube.

Preferably, the antibody coated support may be further coated with an inert protein, such as casein or albumin to block substantially all remaining binding sites on the support and thereby suppress nonspecific binding of tracer directly to the support. Blocking with an inert protein is conventional in the immunoassay art.

A solution suspected of containing an antigen is added, and conditions conducive to binding the antigen to the antibody are provided. (In this disclosure, antigen bound to antibody is hereinafter called the bound fraction.) A tracer including a second antibody having a peroxidase covalently conjugated thereto is added. After binding of the second antibody to the antigen, the solid support having affixed thereto an antibody-antigen-peroxidase-labeled antibody bound fraction is contacted with a solution containing peroxide and the substrate of the invention. The substrate is oxidized by the peroxide in a reaction catalyzed by the peroxidase component of the bound fraction on the solid support to form a color. The color is indicative of the presence of the antigen and the intensity of the color is directly proportional to the concentration of the antigen in the liquid.

In a typical competitive assay of the invention, a limited quantity of the antibody on the solid support may be contacted with the liquid suspected of containing the antigen and a tracer which includes a known quantity of the antigen having peroxidase conjugated thereto. The antigen and enzyme-labeled antigen bind to the antibody on the support in direct proportion to their concentrations in the solution. Thus, after binding, the support contains an antibody antigen bound fraction and an antibody peroxidase labeled antigen bound fraction. After separation of the support from the assay fluid phase, the bound fractions on the support may be contacted with peroxide and the substrate of the invention to cause formation of a color. However, in the competitive assay of the invention, the color formed is inversely proportional to the concentration of antigen in the liquid.

It is evident from the above discussion that the substrate of the invention may also be used in an assay for a peroxidase in a liquid. In this embodiment of the invention, a liquid suspected of containing a peroxidase may be contacted with peroxide and the substrate of the invention. Formation of color in the liquid is indicative of the presence of peroxidase, and the intensity of the color provides a measurement of the concentration of the peroxidase.

In still another embodiment of the method of the invention, the substrate of the invention may be used to determine a peroxide in a liquid. For example, a sandwich immunoassay for an analyte may be performed on a solid support using as the label an enzyme, such as glucose oxidase, which releases hydrogen peroxide into the assay fluid phase at a rate proportional to the glucose oxidase concentration. Measurement of the hydrogen peroxide released may be carried out by adding HRP and the substrate of the invention whereby the peroxide may be determined by the color formed and may be related to the analyte.

In the preferred immunoassay embodiment of the invention, an antianalyte is affixed by either covalent bonding or physical absorption to a membrane. Suitable membranes are, for example, nitrocellulose membranes and IMMUNODYNE ™ nylon membranes (Pall Corp., East Hills, NY).

When the solid support is a membrane, the substrate of the invention provides more sensitive visual detection of HRP (i.e., a visible colored spot forms on the membrane at a lower concentration of HRP) than with any prior art substrate. In addition, the colored spot formed with the substrate of the invention is stable and cannot be washed off the membrane, in contrast to the spots formed with prior art substrates such as OPD.

The following examples are provided to further illustrate the invention but are not to be considered in any way to be limitative of the invention.

EXAMPLE I

Ten μg of anti RSV antibody in 2 μl of carbonate buffer (50 mM, pH 9.5) were applied to an IMMUNODYNE ™ nylon membrane with a micropipette. The membrane was incubated with a TRIS buffered solution of casein to block the remaining sites, and dried. The membrane was assembled into a device which allows liquids to be passed through the membrane and into an absorbent pad. Serial dilutions of a 300 ng stock of RSV infected HEp-2 cells were prepared in a buffer containing TRIS, sodium chloride, EDTA and a detergent. 150 μl of this material was passed through the membrane. Another antibody coated membrane was treated with 300 ng of uninfected cells as a control.

The membranes were washed with TRIS buffered saline (TBS) and incubated with HRP conjugated anti RSV monoclonal antibody in TRIS containing casein. After two washings with TBS buffer, the membranes were treated with citrate/phosphate buffered (pH 5.0) solutions of DAT and DAB (2 mg/mL) containing hydrogen peroxide. After a five minute incubation, the enzymatic reaction was stopped by the addition of TBS, and the intensity of the colored spots was compared using a densitometer (Model 183, Gretag Ltd., CH-8105 Regensdorf, Switzerland). The background control substracted results of this experiment are presented in Table 1 in arbitrary units of color density.

TABLE I

| Substrate | Ng. of Infected Cells | | | | Control |
|---|---|---|---|---|---|
| | 300 | 100 | 33 | 11 | |
| DAB | .07 | .04 | .03 | .04 | 0 |
| DAT | .82 | .57 | .37 | .28 | .24 |

It is seen that, even with 300 ng of infected cells, the prior art substrate, DAB, gave a barely perceptible color reading on the densitometer. In contrast, the DAT substrate of the present invention gave stable, deeply colored spots well above control values down to 33 ng of infected cells.

EXAMPLE II

Comparison of Substrates for HRP Detection on Membranes

Horseradish peroxidase was diluted serially in 10-fold steps in a buffer containing 51 mM phosphate, 24 mM citrate, pH 5.0. Spot volumes of 1 μL of each stock were applied to either nitrocellulose (0.45 micron, Schleicher and Schuell) or IMMUNODYNE ™ nylon immunoaffinity membrane (5 micron, Pall). The membranes were allowed to air dry and then immersed in filtered substrate solutions containing 2 mg/mL of substrate compound and 0.68 μL/mL of 30% hydrogen peroxide in citrate/phosphate buffer. The reaction was quenched after approximately three minutes with a water rinse. The colored spots were quantitated with a reflectance densitometer (Gretag model 183). The results are presented in Table II in arbitrary units of color density.

TABLE II

| | Amount of HRP | | | | |
|---|---|---|---|---|---|
| | 0.3 mg | 30 ng | 3 ng | 0.3 ng | 30 pg |
| Nitrocellulose membrane | | | | | |
| A) 3,4 Diaminotoluene (DAT) | .38 | .28 | .10 | .09 | .03 |
| B) 4,5-Dimethyl-1,2-phenylenediamine | .55 | .43 | .22 | .11 | .03 |
| C) 4-Chloro-1,2-phenylenediamine | 1.25 | .87 | .55 | .26 | .09 |
| D) 4,5-Dichloro-1,2-phenylenediamine | .60 | .43 | .31 | .10 | .02 |
| E) 3,3',5,5'-tetramethylbenzidine (TMB) | .09 | .09 | .08 | .04 | .01 |
| F) 3,3'-diaminobenzidine (DAB) | 1.03 | .43 | .22 | .04 | .00 |
| IMMUNODYNE ™ nylon | | | | | |
| A) 3,4 Diaminotoluene (DAT) | .99 | .85 | .54 | .21 | .04 |
| B) 4,5-Dimethyl-1,2-phenylenediamine | .53 | .50 | .22 | .05 | .00 |
| C) 4-Chloro-1,2-phenylenediamine | 2.24 | 1.89 | .68 | .12 | .06 |
| D) 4,5-Dichloro-1,2-phenylenediamine | .48 | .41 | .10 | .00 | .00 |
| E) 3,3',5,5'-tetramethylbenzidine (TMB) | .23 | .19 | .11 | .00 | .00 |
| F) 3,3'-diaminobenzidine (DAB) | 1.67 | .78 | .22 | .04 | .00 |

Thus, the invention provides new peroxidase substrates which give deeply colored oxidation products in the presence of peroxide and a peroxidase. The oxidation products have a solubility such that deeply colored solutions or, preferably, stable spots on solid phases are obtained. Improved peroxidase-based assays are obtained by its use.

What is claimed is:

1. A method for determining an analyte in a liquid comprising:
    a) contacting a liquid suspected of containing an analyte with an antianalyte affixed to a solid support and a tracer including a second antianalyte having a peroxidase conjugated thereto whereby a bound fraction which includes said peroxidase is formed on said support;
    b) contacting said support with a liquid containing peroxide and an o-diaminobenzene having a substituent in at least one of the 4 and 5 positions selected from the group consisting of a lower alkyl group of 1 to 6 carbon atoms and a halogen atom, the peroxidase portion of said bound fraction catalyzing oxidation of said o-diaminobenzene by said peroxide; and
    c) determining said analyte by the appearance on said solid support of a stable insoluble colored spot formed by said oxidation.

2. The method of claim 1 wherein said analyte is selected from the group consisting of an antigen, antibody and hapten.

3. The method in accordance with claim 1 wherein said antianalyte is an antibody.

4. The method in accordance with claim 1 wherein said tracer comprises a component selected from the group consisting of an antigen and an antibody.

5. The method in accordance with claim 1 wherein said solid support is selected from the group consisting of a membrane and a dipstick.

6. The method in accordance with claim 1 wherein said determining step includes measuring said color and comparing the intensity of said color with the intensity of color formed when steps (a) and (b) are repeated with a liquid containing a predetermined quantity of said analyte.

7. A method for determining an analyte in a liquid comprising:
   a) contacting a liquid suspected of containing an analyte with an antianalyte affixed to a membrane and a tracer including a peroxidase whereby a bound fraction which includes said peroxidase is formed on said membrane;
   b) contacting said bound fraction with a liquid containing peroxide and an o-diaminobenzene having a substituent in at least one of the 4 and 5 positions selected from the group consisting of a lower alkyl group of 1 to 6 carbon atoms and a halogen atom, the peroxidase portion of said bound fraction catalyzing oxidation of said o-diaminobenzene by said peroxide; and
   c) determining said analyte by the appearance on said membrane of a stable insoluble colored spot formed by said oxidation.

8. A method for determining an antigen in a liquid comprising:
   a) contacting a liquid suspected of containing an antigen with a first antibody affixed to a membrane and with a second antibody having a peroxidase conjugated thereto whereby a bound fraction which includes said antigen, said antibodies and said peroxidase is formed on said membrane; p1 b) contacting said bound fraction with a liquid containing peroxide and 3,4-diaminotoluene, the peroxidase portion of said bound fraction catalyzing oxidation of said 3,4-diaminotoluene by said peroxide; and
   c) detecting said antigen by the appearance on said membrane of a stable insoluble colored spot formed by said oxidation.

9. The method in accordance with claim 8 further comprising measuring the concentration of said antigen in said liquid by measuring the intensity of said color and comparing said intensity with the intensity of color which forms when steps (a) to (c) are repeated with a liquid containing a predetermined quantity of said antigen.

* * * * *